United States Patent
De La Llata Romero

(10) Patent No.: US 8,545,900 B2
(45) Date of Patent: Oct. 1, 2013

(54) METHOD OF OBTAINING TOTAL FIXED LIPIDS FROM SEEDS OF THE SAPOTACEAE FAMILY, FOR THE PREPARATION OF COSMETICS AND DERMATOLOGICAL PHARMACEUTICAL COMPOSITIONS

(76) Inventor: Luis De La Llata Romero, U. Hab. Villa Olimpica (MX)

( * ) Notice: Subject to any disclaimer, the term of this patent is extended or adjusted under 35 U.S.C. 154(b) by 1307 days.

(21) Appl. No.: 11/632,960

(22) PCT Filed: Jul. 21, 2004

(86) PCT No.: PCT/MX2004/000051
§ 371 (c)(1),
(2), (4) Date: Mar. 11, 2009

(87) PCT Pub. No.: WO2006/009417
PCT Pub. Date: Jan. 26, 2006

(65) Prior Publication Data
US 2009/0197839 A1    Aug. 6, 2009

(51) Int. Cl.
*A61K 36/00*    (2006.01)
(52) U.S. Cl.
USPC .......................................................... 424/725
(58) Field of Classification Search
None
See application file for complete search history.

(56) References Cited

PUBLICATIONS

Takeda et al. (Constituiton of lucumin and its related glycosides from Calocarpum sapota Merill, Chem. Pharm. Bull 45(4), 697-699, 1997).*
Bondioli et al. (Chemical Characterization of Sapota (*Lucuma mammosa*) seed, Rivista Italiana delle Sostanze Grasse (1996), 73(5), 229-230, see abstract).*
Mohamed et al. (Physical, morphological and chemical characteristics, oil recovery and fatty acid composition of *Balanites aegyptiaca* Del. kernels, Plant foods for Human Nutrition 57, No. 2, pp. 179-189, 2002).*

* cited by examiner

*Primary Examiner* — Terry A McKelvey
*Assistant Examiner* — Randall Winston
(74) *Attorney, Agent, or Firm* — Welsh Flaxman & Gitler LLC

(57) ABSTRACT

Procedure for the obtaining a concentrate of the total fixed lipids of the kernels of the family Sapotaceae, genus *Calocarpum*, *Chrysophyllum* and *Lucuma*. The kernels (seeds removed of the endocarp), are squeezed by means of mechanical techniques that use pressure and heat, without using extractive liquids, getting a concentrate of lipidic juices (virgin) in a dry way and with their characteristic aroma. This concentrate of total fixed lipids can be fractioned in its main constituents by means of a process that consist of the emulsification of the lipids, followed by centrifugation or sedimentation, giving place to the stratification of the main constituents and their consequent separations. The main constituent consist of oils, of phospholipids and of residues glucosidic triterpenes plus of sterols fractions. These fraction or as a whole concentrate are used to prepare cosmetics and pharmaceutical compositions of topical application, to act in the skin like anti-seborrheic, healing, promoter of delicate defoliation and as invigorated epithelia regeneration agents, as cutaneous anti-wrinkle agent and as adjuvant in the development of the hair.

8 Claims, No Drawings

METHOD OF OBTAINING TOTAL FIXED LIPIDS FROM SEEDS OF THE SAPOTACEAE FAMILY, FOR THE PREPARATION OF COSMETICS AND DERMATOLOGICAL PHARMACEUTICAL COMPOSITIONS

BACKGROUND OF THE INVENTION

The expression, the act of squeezing is a process of forced separation of the liquids of some solid by the use of some mechanical principles as the pressure, as those used in some obtaining of fatty substances starting from seeds.

The present invention is related with the process of obtaining the expression products, the fixed total lipids and as an alternative method the extraction with extractive liquids, of the oils, of the fruits seed, removed from the pericarp thru the endocarp (the kernel) of *Calocarpum, Chrysophyllum* or of *Lucuma* (the "sapotes"), plants of the family Sapotaceae, and its use in cosmetics and pharmaceutical compositions, with antiseborrheic properties; resolved for the purpose of promoting the defoliation and renovation of the skin with the renewal growth or development of the epidermis and to counteract the epidermal aging, the premature deterioration of the skin and the hair, in topical preparations. These fixed total lipids, included the oils together with the sapogenins of same *Calocarpum, Chrysophyllum* or *Lucuma* which show up to harness the percutaneous penetration and of other effects described in the obtaining of the cyanogenic and related glycosides; and their derived genin and sapogenins.

These modified said technique of expression of the fixed total lipids a reason of the present invention, is a reformed process with which the total group of fixed lipids (non volatile, total lipids in composition) are obtained of *Calocarpum, Chrysop hyllum* or *Lucuma*; in purer form (virgin), without the use of extractive liquids in their obtaining and with its characteristic aroma, thing that it's not gotten in the conventional processes of expression or of extraction with solvent. This last extractive process is required in this work and in the subsequent one, if it's wanted to arrive to the complete separation of the lipids of the solid residue of expression, in a second subordinate process of obtaining of the entire oleaginous phase to fullness, in the integral use of the kernel.

It is an objective of the present invention is to solve the problem of the extraction of the said oils and in other ways of obtaining of these in rudimentary, traditional achievements, handmade of the same ones that are related with the most recent, latest state of the technique; that are embraced inside the present work in different form. In this work the form of obtaining of the fixed total lipids, which are gotten by mechanical means starting from the related *Calocarpum, Chrysophyllum* or *Lucuma*, to be used in cosmetics and dermatologic products that include to the mentioned "sapote" oils. In the antecedent techniques to this invention by extraction the oils were gotten but not the total fixed lipids as in the present invention, the same thing happens by other usuries and rustic avails not well achieved of preparations that are in continued practices in cosmetics, medicinal and nutritious traditional uses, that distinguish the beneficial effects in the skin, the hair and in other affections and uses with the help of arrangements of the oils of *Calocarpum*, of *Chrysophyllum* or of *Lucuma* without ending up in the discoveries of the mechanical technique of their obtaining, coupled up with other discoveries of obtaining, isolations and properties of extracts and substances of chemical similar properties that are obtained here. With the new modified technique of expression proposed here, a reason of the present invention, a wider portion in variety of different lipids are obtained (of what the oils or fatty acids are belonging to the extraction process); the fixed total lipids, constituent of the total liquid portion of expression of this new technique proposed that comprise the glycerides and fatty acid (the oil), besides the phospholipids fraction (included the lecithin of the "sapotes"), further other lipidic like fractions of residues triterpenic glucosides and of sterols that are embraced inside the fixed total lipids or to the composition of the whole lipids of expression of the "sapotes", components of the entire group in union or the complete lipidic portion obtained, being an integral total part of the fixed lipids belonging to the "sapotes" that are obtained in this process by expression, to be used in cosmetics and dermatological products, existents alternating substitutes in uses or in potential feasible uses, as such or in other form of the main constituent fractions separated, mentioned previously.

As second part of the objectives of this application it's that of the same new technique of obtaining of the fixed total lipids from the modified process of the lipidic expression (and also from the lipidic extraction) together with the biological uses that are given to the products by the present work of which some are described in this application but they don't imply to be restrictive in the examples presented here and in their wider uses in the practices as the one of incorporating them in cosmetic preparations or active pharmaceutical dermatological preparations, effective and novel that are efficient for the delicate defoliation (desquamation) of the stratum corneum, horny (keratinized) superficial layer, by means of the progressive, gradual renovation of epidermal layer and as healing agent and antiseborrheic; or as substitutes in existing or potentials uses The purpose is to put these products with the total fixed lipids principles of *Calocarpum, Chrysophyllum* or *Lucuma* within reach of the public in ingenieriles forms in industrial mediating transformations of application, which solves the technical problems in the traditional obtaining and of the extraction of oils with solvent, avoiding the employment of extractive liquids difficult to remove and residuely harmful and the inherent biggest cost in the employment of these last ones and its ulterior separation to completeness (energy expenses and of manipulation to get the solvents in pure state, expenses practiced for the integral removal of the liquid of extraction to the oils or strange scents of solvent, plus energy consumption for evaporation or separation of the solvent, energy expenses of recovery of the solvent, etc.).

Another improvement that it is a fact, it's on the techniques in the traditional medicinal uses, cosmetics and nutritious, that is their employment and obtaining in an entirely more satisfactory way and of rational uses of not well used resources that in their uses in rudimentary, rustic treatments or like vegetable matter of waste or like extractive product, with expensive solvent.

Another improvement of the techniques proposed here is its entirely employment and obtaining in a more satisfactory way and of rational use of the origin resources, of the resulting materials and of the elaborated products obtained and, against utilities not well developed in applications of traditional medicinal, cosmetic and nutritious practices in rudimentary, rustic treatments or for handlings and obtaining by extractive procedures (with solvent), with different attaining to the total fixed lipids of the obtaining here proposed in registration, by different achievements that involve other materials that increase the cost of the resultant raw material, or what is worse that the vegetable spare matter of the fruit (the seed) that is not used, be as a useless waste.

The state of the technique says that of the kernel (the removed seed of the endocarp) there are extracted between 45 to 60% of a whitish substance similar to the vaselina semisolid which is eatable when recently "extracted" and refined (the extraction is a process that uses liquids or solvent in its obtaining), or the semisolid oils. There are sometimes used in soaps and it is considered to have great potential in the soap industry, in that of cosmetics and in pharmaceutical products. In Santo Domingo, this oils of extraction of the kernels are used like ointments for the skin and in cures for the hair, mentioned in the previous reference.

In remote regions of the central of Mexico and of more to the south they are used as medicinal remedies, cosmetics and nutritious in traditional employment that uses the prepared vegetable matter of *Calocarpum, Chrysophyllum* or *Lucuma* especially the kernels of the seed (and germinated cotyledons) in fresh state or dry off in diverse traditional uses.

The traditional knowledge confers to the oils of the common sapote, *Calocarpum sapota* or to *Lucuma mammosum* promoter activity of the growth of the hair, however studies in the University of California in Los Angeles (1970), by means of clinical tests practiced to the oils, fail in finding this activity (not finding), but they confirm that the oils of *Calocarpum sapota* are effective to stop the fall of the hair caused by seborrheic dermatitis. However the author of the present work has found this activity with respect to the growth of the hair with the total fixed lipids acting synergistically with another extractive fraction of the kernels of *Calocarpum, Chrysophyllum* or *Lucuma* that correspond to some derived cyanogenic glycoside and related as the sapogenins that are reason of another patent application related by the same author.

The fixed "oils" also have employments with sedative effects in illnesses of the eyes and of the internal hearings ear. The "oil" of the kernels is considered as digestive, also the "oil" of *Calocarpum* or of *Lucuma* it is said to be diuretic.

Traditional cooking recipes that use as substitute the milled kernels of *Calocarpum* or *Lucuma* in the preparation of bitter chocolate exist but like traditional food without processing to separate of the toxic glycosidic matter, not eatable, limits their consumption because it contains a cyanogenic substances.

Of the kernels the fixed lipids are obtained (included the oils), they are eatable and these is why it is used as nutritious complement in the traditions described previously (as well for their aroma), but their high fusion point makes them not very recoverable form the conventional or traditional adequate expression techniques or from extraction and this way making not easily to be separated from the vegetable matter or of the kernel waist pulp (bagasse) profitably or separated of the cyanogenic compound present and being used with more potentiality in industrial diverse uses.

The fruit of *Calocarpum* and *Lucuma* have many uses in the traditional cooking and of economic considerable rate and the non consumable parts as food, as the kernel, have diverse uses in rustic traditional cosmetic, nutritious and medicinal preparations which don't end up separating the principles and identify the particular effects in isolated form or to separate the toxic compound and to enable to some present substances as to the oils or fixed total lipids, phospholipids or lecithin, of the "sapotes" in an economically convenient way. The kernels not consumable traditionally or used as breeding foot which is a minimum part, the rest is of waste of the consumption of the commercial or rural fruits.

The cosmetic or pharmaceutical dermatological preparations according to the invention contain the active compounds preferably, the fixed total lipids in such a form or like oleaginous united mixture or in fractionated form, made up of the fixed oils, phospholipids and residues triterpenic glucosides (non cyanogenic), plus of the sterols (as the lupeol, the $\alpha$- and $\beta$-amirin, sitosterols, cholesterols, and different lanosterols and related triterpenes corresponding to the acrimonious matter of the total fixed lipids obtained by these modified expression which gives the characteristic aroma of kernels or aroma of the same fruits to the hole portion of fixed total lipids to, substances that belong to the triterpenic glycosidic extract and of sterol recovered of the fixed total lipidic portion of expression of the "sapotes." These the sterols and acylsterols and residues triterpenic glycosides, (which are different to the cyanogenic and similar related glycosides) have ester unions in the fatty acid associated to the alcoholic group of the sterols, weak to the amyloidal structure of the kernels and which are obtained by means of the modified process of expression proposed by this work. Obtained by this process of lipidic expression the previous insaponificable matter included in the fixed total lipids, is collateral alternating in the effects of the "sapotes" that together with the sapogenins, genin, glycosidics extracts structurally related to the cyanoglycoside (similar related glycosides) or the cyanogenic glycoside as so of the "sapotes" and their obtaining form and uses in cosmetic and pharmaceutical dermatological preparations, being the last four substances reason of another patent application from the same author (ref. 30) and the attainment of the mentioned effects that in group of these effects comes from the kernels of *Calocarpum*, of *Chrysophyllum* and of *Lucuma* that are claimed by this work.

The object of the present invention is to solve the inherent problem of the process of extraction of the oils of the "sapotes" since these are obtained with solvents, offering as alternative the innovation in the form of obtaining to the fixed total lipids by means of the modified lipidic expression presented here and its use in cosmetic and pharmaceutical dermatological preparations or in alternating substitutes, existent and or potentials uses.

The oils of the "sapote" are obtained in handmade form at the present time or by extraction with solvent and they have been used in the preparation of ointments.

The reason of the present invention application consists of a mechanical simplified process to obtain oils with in the fixed total lipids by means of the modified expression technique with which it is obtained more then that of fixed oils fraction, obtained in extraction; in expression two other main fractions are obtained, that are the phospholipids fraction and a fraction of insaponificable matter recognized as sterols or by residues triterpenic glycosidic alcohols or the sterile and acilesteril glycosides; and the use of all these products of the lipidic expression, in whole (total) form or fractioned in their components in cosmetics and pharmaceutical dermatological compositions and in alternating substitutes or potentially existent uses.

SUMMARY OF THE INVENTION

The expression process a main reason of the present work has as technical advantage with regard to the predecessor extraction processes, that these is obtained in pure form and that they are achieved at a smaller cost since the process is reached without introducing increasing expense, estrange liquid (in the attainment of the extractive matter) and the lipids being obtained in "virgin" pure state. This is that they are achieved with the saving of the rising price of the extraction process and of the ulterior separation of the extractive liquids and the recovery of these. The total fixed lipids of the invention are obtained in dry form, without water or with other strange liquids and without strange scents and with the characteristic aroma of the kernels by the modified process of lipidic expression proposed in this work.

The kernel of the common sapote contains near the 30 to 60% of lipids in gross form in dry weight like it was said previously, of which is obtained between 35 to 95% of this first rough total content of fixed lipids of the vegetable (kernels) matter, by these unique modified process of expression, here manifested and one reason of the present invention in "virgin" pure form and the remainder of non recoverable lipids by means of the previous process is feasible to be recovered by means of the technical linked extractive lipidic (product) recovery of the residue solids of expression, by extractive means, as having described previously and later on. Being this the reason for including these extractive techniques in this application of innovation registration, in the integral recovery of the oleaginous fraction of these related plants.

Besides the total fixed lipids obtained by expression, like it's described later on and a reason of this application is that it is possible being fractioned expedite in its main constituents. These are in the fraction of fixed oils, the phospholipidic faction including the lecithin, and by a fraction of a group of solid lipidic insaponificable matter that corresponds to sterols and residues of sterile and acilesteril glycosides obtained by this process.

The fraction of solid insaponificable lipids corresponds to a group of substances that are obtained in the process of lipidic expression of the present invention that include the triterpenic alcohols as it's admitted in this work and in that of other investigators as residues glucosidic sterols or the sterols in free form or in esterified form, forming the sterols and the free acylsterols or together to the glycosidic portions with weak unions to the amyloidal portion of the kernels. These substances are recognized to belong to chemical groups as to the cholesterols, sitosterols, stigmasterols, lanosterols, lupeol, including to the α- and β-amirin.

The fixed oils in the conventional form of obtaining in general by extraction, depending on the liquid phase that it's used like extractive means and which it has to be by a nonpolar liquid (solvent) in pure form, which drags the lipidic matter of the solid vegetable selectively of the kernels and after the refinement process it is obtained like oils, by filtration in the process, these being able to be the method of main purification which retains the glucosidic triterpenic composition and of the sterols, sticky retained in these means. In the extractive processes for the obtaining of the lipids like the oils and in the extractive proposed as degreasing practiced mean to the solid residues of expression alternating or subordinate process as is referred later on a more reduced fraction of the fixed total lipids it is obtained to that of the one obtained with the process of the lipidic expression of *Calocarpum*, of *Chrysophyllum* or of *Lucuma* proposed here. In these extractive processes with solvent it's gotten different proportions of the fixed lipidic components, contrary to the process of obtaining of the fixed total lipids by the modified expression presented in this work. The resulting lipidic obtaining in the extractive existent processes and those here presented, get a smaller portion in composition because of difficulties in the intermediate and final isolation recovery of the members of the fixed lipids of extraction, mainly for problems in the filtrations of the residues glucosidic triterpenic alcohols and of sterols among other joined to solid residues that obstruct the filtration pore blocking the recovery of these same substances reducing the composition of the same lipidic fraction by retention. In this solid/liquid extractive process a greater percentage of oils it is obtained (from 40 to 95%) and a minimum part of phospholipids (from 5 to 60% depending on the thoroughness in the work that you had carried out) of the lipidic filtering liquid in dried weight, and the sterols or sterile and acylsteril glycosides or free or glycosilated triterpenic alcohols is not obtained or a minimal part of fraction is obtained, contrasted with the modified expression process of this invention (that it is the main reclamation of the present application) that obtains the phospholipidic fraction in more proportion (from 30 to 60%) and also obtains the residues triterpenic glucosides and the sterols fraction (from 0.1 to 1% or more) in the fixed total lipidic mixture; the oils fraction is obtained as the majority fraction (from 40 to 70%) of the filtering lipidic liquid in dried weight in form of a fraction, which are integral of reasons of claims of this invention.

In the modified process of lipidic expression that is a reason of the present invention and that it consists on the form of obtaining the fixed total lipids from this mechanical method that is described later on present work that uses pressure plus heat in the obtaining of the fixed total lipids and that these and their components in an isolated form or in conjunction total form with the solid remainder of expression, or the solid residue product of this process (see ref. 30) and of the subordinate process of lipidic extraction that we will name in this way in the successive, are the main claim of this application.

In the extractive process that use solvents proposed in the present invention for the complete separation of the lipids of the solid residue product of the expression of the kernel, linked alternatively to the main previous process of lipidic expression of this application there are obtained from the 50 to 99% as yield of fixed lipids of the total content of fixed lipids of the solid residues of the expression.

Of the total quantity of lipids obtained by means of the unique process, manifested here of the modified expression, coming from the kernels that are mentioned in previous and in later paragraphs, it's characterized because it is possible to fractionate from a 40 to 70% of fixed oils and from 30 to 60% of phosphatidic matter of the total lipidic content of the kernels (depending on the composition of the fixed totals lipids present and of the thoroughness in the division of the gravitational stratification [centrifugation] that are done). Of the previous mixture of fixed lipid (oil plus phospholipids) there are extracted approximately from 1 to the 0.1% of non saponificable solid matter corresponding to the fraction of residues glycosidic triterpenes, the sterile one and acylsteril glycosides and of free sterols that give there own characteristic with their peculiar aroma of total fixed lipids of the vegetables, obtained by this modified expression process presented now in this work that correspond partly to the matter acrimonious or the matter that gives the aroma and other properties to the total lipidic portion of the kernels. The separation of the referred total fixed lipids is described in the example 3, and it's achieved by means of the emulsification with 50 to 300% of water approximately, for the later break up of the emulsion with the employment of centrifugation of 230-8,000×g (or grater gravities) for 5 to 45 minutes (or for more prolonged time) (Koenig 1982). The different mentioned lipidic fractions obtained by centrifugation are separated whit in the stratifications, or by using the spontaneous partial separation due to difference in the specific gravity of the fractions. If the last spontaneous process is use it should be repeated in the With this process of obtaining of the fixed total lipids, by modified expression presented in this work, the oils are obtained and the phospholipidic fraction is gotten in a grater concentration that with the extractive process, with solvent. With the previously mentioned extractive precedents processes and with the similar processes here presented as alternating or subordinate method of the main process of expression, a smaller concentration of the phosphatidic matter are obtained. The same thing happens with the insaponificable matter fraction considered as the residues of glucosidic sterols, free sterols and acylsterols or they are not obtained at all, in contrast with the modified expression process here presented. The last mentioned fraction is the one that gives the characteristic aroma to "sapotes" kernels to the modified fixed total lipids of expression of the invention manifested here that get them concomitantly in higher yields, as said previously, contrasted with the extraction process with solvent.

The main process matter of the present invention confers characteristic to the products of the lipidic expression, the fixed total lipids, which include three main lipidic fractions, two preponderant fractions with regard on the concentration that are that of oils and that of phospholipids and a smaller fraction or of insaponificable material corresponding to the residues glucosidic triterpenes and sterols, as it was said previously.

Other characteristics of the products of the modified lipidic expression presented here are the biological properties that are gotten in the cosmetic use and in dermatological preparations or as substitutes, in different utilities existents (or potentials) as for example the use of "sapote" lecithin in nutritious uses or like raw material in pharmaceutics.

The total fixed lipids obtained by the expression process described here present two preponderant portions, the fraction of oils and to the phospholipids fraction made up of a third fraction consistent of 1 to 0.1% (approximately) of insaponificable matter considered of the "sterols" fraction with the sterile and acylsteril glycosides (or the residues glucosidic triterpenes), which form this total lipidic mixture which is characterized by the obtaining process and in such a way as these substances are gotten, obtained by modified expression of lipids that is the form of obtaining the lipidic juices of the vegetable matter (kernels) using heat and pressure by mechanical means as it is described later on or by the same principles described in the literature, with the limitations in their developments for diverse circumstances, partially related in the reference 15; like in contrast with the modified machines of this invention, modifications here described in this present work by partialities that are altered in technical modifications by consistent transformations in a graduate thermal device in the "line" of the squeeze packing that reaches temperatures between 80 and 110° C., and at least pressures of $12.5 \pm 4.5$ pound/feet$^2$ equivalent to $59.85 \pm 21.55$ Newton/meter$^2$ practiced in the matter preferably cut, triturated or sliced or as a whole which are capital reasons of claims of the present application. This modified technique as in the present invention can be achieved with the same triturating mechanisms, packing and of pressure of similar operation with the existents gears for expression partially developed at the present time of the previous appointment coupled with a thermal graduate devices that reaches temperatures from 80-110° C.

The vegetable matter is selected of the kernels of the "sapotes" of one of the related species which are cut (slices, crushed or as a whole) with the purpose of diminishing its volume and can enter in the modified mill as having said previously, to the specified temperature and a same or grater pressure to the one mentioned previously that are reasons of claims of the present invention.

The process of obtaining of the fixed total lipids by expression is in a novelty, as inventive activity, scalable at industrial levels and the obtained products are different from the oils that are manifested in the reference 1 and with some properties like already well-known and said in the same reference, as that of preparation of ointments, and the anti-seborrheic activity of the oils and its high potential in the industry of the soap, pharmacist and of cosmetics and nutritious and chemical industry in general (ref. 1, 27).

The common sapote or *Calocarpum sapota* or *Lucuma mammosa* and the related "sapotes" in the present description contain a toxic substances in the kernels, the lucumina that is a cyanogenic glycoside present in the family Sapotaceae (also in the genus *Chrysophyllum* of the same family that make the kernels be not edible, contrary to the pulps of the fruits, however the expression like process of obtaining of the fixed total lipids (of the kernels), detoxifies, isolating them and obtained with their characteristic aroma of the kernels, being dragged perfumed substances of residues glycosidics of sterols and acylsterols, leaving united in the solid residue of trash the cyanogenic glycoside and related glycosides structurally similar, eliminating the toxic material in the solid remainders (solid residues) of expression of the total squeezed lipids of the kernels.

For these exposed reasons with this process of obtaining of the fixed total lipids by expression, here described that gives different characteristic to these fixed lipids obtained by this main process of the invention together with the biological effects that are also jointly reasons of claims in this invention with their properties in form of total lipidic portion or in their fractions in their main components and the uses in cosmetics and pharmaceutical dermatological compositions or in existents substitutes uses or potentials belong to claims of this invention.

DETAILED DESCRIPTION OF THE INVENTION

The fruits known traditionally as sapotes that corresponds to the soft and sweet fruits of big and lengthened kernels with hard endocarps wrapping the kernels and of reddish (colorado) pulps, rosy (pinkish), yellowish or white that is eatable and their name, sapote is derived of the nahuatl word tzapotl, of the pre-Columbines residents of Mesoamerica of where the species *Calocarpum sapota* Merril originates, also well-known as lúcumo, lúcuma or *Lucuma mammosa* Gaertn. in different regions, with synonymy of *Calocarpum mammosum* Piere, *Pouteria mammosa* (L.) Croquist, *Pouteria sapota, Vitellaria mammosa* Radlk., *Sideroxylon sapota* Jacq., *Achrodelpha mammosa* Cook, *Achras mammosa*, also for *Sapota mammosa* that correspond to identifications of the same species of the big and red sapote. Trivially called tezontzapote, tzapotl, tzapote, sapota, sapote, big sapote, mammey sapota, mammey, red mammey or mammee and other vernacular names correspond to chachaas or chachahaas.

It is also included as representatives of the "sapotes" corresponding to the etnobotánica regions of cultivation as Santo Domingo's sapote *Lucuma domingensis, L. cuprea*; or another species like the Haiti's sapote with denominations of *Lucuma stahliana* or *L. dussiana;*.

Other species of the family Sapotaceae that are also representative of the species of the "sapotes" is the green sapote or sapote implant, denominated *Calocarpum viride* or *Pouteria viride*.

Another species related in the present work are the sapote "borracho" or yellow sapote, the canistel denominated as *Lucuma salicifolia* HBK, *L. campechianum* Baehni, *L. nervosa* Baehni, *L. palmeri* Fernald, *L. heyderi* Standl, *L. laeteviridis* Pittier, *L. rivicoa* Gaertn., *L. multiflora* Millsp., *Pouteria campechiana* Baehni.

Another species linked to the "sapotes" at the present work is those denominated as Lucmo or admitted as *Lúcuma* as *Lucuma sphaerocarpa, L. obovata* HBK., *L. bifera* Molo; with synonymy of, *Pouteria obovata, P. Lucuma*.

Another genus representative and related in their lipidic composition and in the rest of their biochemical integration in the kernel, at the presently work to the "sapotes" are the trees of *Chrysophyllum* as the *Ch. mexicanum* Brandegee and *Ch. cainito* L., admitted with the common names of star, cainito, caimito, purple (morado) caimito, green caimito or yellow caimito and abiu belonging to the same family Sapotaceae with synonymy of Achras caimito Ruiz & Pavón, Pouteria caimito Radlk, *Lucuma caimito*.

Of the previously noted ones as representatives of the "sapotes" are also included the generic well-known synonymies as Vitellaria, as *V. mammosa, V. domingensis, V. salicifolia, V. sphaerocarpa* (ref. 9).

They are native plants of America of tropical and subtropical regions of warm temperate climates, of low humid lands (for exception of *L. obovata* 1500 to 3000 m. of altitude). They are sapotaceous trees that gives big lengthened fruits or round and fleshy clear, yellowish, rosy (pinkish) or red (colorado) pulp, of thick or soft shells and seeds with hiliums in the endocarps, very appreciated traditionally and of economic importance that are distributed throughout Mexico and extends to other parts of the southern (and northern) continent and in other continents in cultivated state for the human consumption, some separated varieties are cultivated as foot implant or it raises and other wild ones.

The present invention is related mainly with the form of obtaining the total fixed lipids of the kernels of the *Calocarpum*, of *Chrysophyllum* or of *Lucuma* from the modified expression, conforming an integral lipidic liquid aggregate at the obtaining temperature, of the total fixed lipids of the related "sapotes".

These fixed lipids that are solid at ambient temperature (<below 20 or semisolids <30° C.), fatty or vegetable butter respectively rich in solid saturated glycerides but also by liquid insaturated glycerides easily oxidizeable by the environment. They are also constituted more by free (and esterificated) fatty acid by Lecithin of the family Sapotaceae included in the phospholipids, coming from *Calocarpum*, of *Chrysophyllum* and of *Lucuma*.

In the kernels of the common sapote there are near 30 to 60% of fixed lipids in dry weight as mentioned previously, in the other species of the related "sapotes" in the present work there are intermediate quantities of these fixed lipids or by consequent differences to the maturation of the fruit. The fixed oils are characterized to be isolated as mixture of lipids conformed by different compounds of oleaginous characteristics and of similar solubility properties that exist especially in the vegetable matter in the kernels in dry or fresh state preferably of *Calocarpum, Chrysophyllum* and *Lucuma*. In fresh state it exists enzymes that hydrolyze the lipids when crushed and a lipidic hydrolyzate of different composition is obtained. Mainly the total lipids are conformed especially by glyceril esters and superior fatty acid of different compositions containing from 12 to 20 carbons, as the saturated palmitic, stearic and arachidonic and the insaturated oleic and linoleic (included in the fixed oils) and by phospholipids or by the phosphatidic matter as the lecithin and sterols, acylsterols plus triterpene glycosides. The first two fractions of lipids, oils and phospholipids are also obtained by extraction techniques with apolar solvent, as alkanes, aliphatic or alicyclic hydrocarbons, and ethers. Preferably in this invention the techniques of lipidic extraction, as a subordinate method or alternate to the main lipid expression of this work, chlorated alkanes are used like they can be the metylene chloride, the chloroform, the carbon tetrachloride or of the dichloroetylene or preferably by the modified expression techniques preceding the first ones for the obtaining of the entire the fixed lipids, in the integral use of the oleaginous phase of the kernels as it is shown in the examples 1 and 2; and to the separations of these in their main constituent fractions in the example 3 respectively.

The starting is from vegetable matter with least commercial value as the kernels of waste of the commercial or rural fruits. These last ones are used removed of the pericarp and endocarp. The vegetable matter is selected of which have changes in the coloration due to oxidation or to the degradation with saprophytic flora caused by excess of humidity. Of this selection they are dried off, they are chopped in small pieces, they are degreased like it was indicated previously by means of expression with which their are obtained the lipidic products of expression that is the total fixed lipids included by the oils, the phospholipids and a fraction of insaponificable matter of sterols, acylsterols and residues sterols and acylsterols glycosides; leaving the "crackling" of squeezed residue vegetable matter (or the solid residue of the expression), with some residue lipidic which is treated as explained in the previous section. Successively after the expression process to this last the process the extraction of lipidic with solvent, as a second recovery of the lipidic phase is carried out to terminate the degreases to an end as is demonstrated in the example 2; and the separation of the lipidic fractions by means of the second subordinate process of extraction is demonstrated by the example 3. The degreased residue of the previous treatment (or the degreased flour or the solid product of the lipidic extraction [or also the residue solid product of the expression]), it's used as raw matter in the obtaining of the cyanogenic glycoside and related similar glycosides to the cyanoglycoside and of their derived genin and sapogenins that are reason of another application of related patent (ref. 30) by the same author.

The total fixed lipids are formed by 3 main lipidic fractions of which 2 are preponderant with regarding their concentrations that are: the fraction of the oils and the fraction of the phospholipids. These two preponderant fractions are also obtained by extraction with solvent but in different proportions (that in the first lipidic modified process of expression of the present invention, example 1). The lipidic extraction as a subsequent process in the treatment of the solid residues (solid residue product of expression,) to remove the remainder of lipids (and leaves other recoverable products), which are feasible their integral obtaining as it is demonstrated in the example 2.

The fraction of oils and the phospholipidic fraction as the predominant fractions, plus to another smaller fraction made up of residues glycosides formed by glycosilated triterpenic compound and of free sterols as they are obtained in the example 1 and they are separated as constituents by the example 3, and their use in the preparation of cosmetics or dermatological pharmaceutical preparations resolved as defoliating agent that promote the progressive renovation, gradual of the skin and the stimulation of the development of the epidermis as exposed in example 5. The portion of total lipids or in fractions exhibits anti-seborrheic effects and healing agent, to combat the effects of the epidermal aging and the premature deterioration of the skin and the hair in topical preparations with synergistic activity that hardens the percutaneous penetration. The property of hardening the percutaneous penetration of a lipidic phases is exhibited together with a watery solution, in dispersed form formed by the oils, phospholipids and or by the fraction of residues glycosidic triterpenes plus that of the sterols or by the total fixed lipids as a whole of the "sapotes" forming a hydrated lipidic laminated phase or by vesicles of the liposomal type of the "sapotes". The hydrated lipidic phase can also be included by different material than those referred lipids of the present invention of the "sapotes", that can imply soluble materials or suspendibles in water as the genin and or the sapogenins or related glycosidic matter structurally similar to the cyanoglycoside as exposed in the examples 6, 7, 8, 9, 10 and 11 and of the effects for their reiterated use in treatments of these preparations in the improvement of the skin and the deteriorated hair.

In some variants of the present invention, on the obtaining the total fixed lipids of the "sapotes" that contain the oils, conformed by triacilglycerides, free fatty acid and also included by a second obtained fraction in the fixed lipids of the "sapotes", that of the phospholipids, of which by treatment with alkalis (alkaline earth metals hydroxides) are transformed by hydrolysis and saponification, mainly to salts of sodium and of potassium, forming soaps as in example 4. The soaps are also formed by the employment of other alkalis as amines, as the trietanolamine or by the transformation of the free fatty acid and esterified in salts of non alkaline metals.

Also the lecithins (or some of the phosphatidic materials of the phospholipids) of *Calocarpum*, of *Chrysophyllum* or of *Lucuma* has a wide potential as an isolated product in the food industry, pharmaceutical and cosmetic. The isolated lecithins of the fixed lipids obtained mainly in this work by the lipidic expression of the present invention, by means of the measured water addition (washes) with which this lipidic fraction "swells with the water", forming hydrates of suspended phosphatidic matter that separate by its specific weight among the superior fixed oils phase being able to solidify by cooling, or to form a colloidal suspension of intermediate material becoming possible the separation of these phases by difference in its specific gravity forming divisions in the stratification. It is allowed the break down of the emulsion with the employment of heat or by the subsequent centrifugation, being able to be with the cooling employment to solidify and to separate, being feasible also the spend of mono or divalent salts in the separation.

The sterols, acylsterols and residues glucosidic triterpene alcohols are separated from the fixed total lipids in the first wash with water or with some polar solvent. The sterols and residues glucosidic triterpene alcohols blur the water mixture forming a colloidal suspension, or a precipitate of this fraction, coming from the fixed lipids of expression, like it is demonstrated in the example 3. One can also separate this insaponificable lipidic fraction using an agent that favors the precipitation of the mentioned colloidal phase of the "sterols" as the digitonin.

According to a second plan the present invention is related subsequently with the preparation of cosmetics and pharmaceutical dermatological compositions developed in particular for the defoliation effects of gradual elimination of the cornuem (keratinized) external superficial layer and the promotion of the gradual renovation of the epidermis, included anti-seborrheic effects; which embrace as compositions with active ingredients to an effective quantity of at least some component of the total fixed lipids of *Calocarpum, Chrysophyllum* or *Lucuma* or its correlated vegetable extracts or corresponding hydrolytic products or as expression products or fraction of some of it, in which are present in an excipient or appropriate cosmetic or pharmaceutical dermatological vehicle; also in this work it is considered the employment of the previous substances of the related "sapotes" in optional uses as existents or potentials substitutes.

Preferably the previously mentioned portion of fixed total lipids; and the lipidic extracts or of oils; or products of the corresponding expression here mentioned or some of the lipidic fractions that it are obtained of the kernels of the fruits seed related to this work, being these the priority of the present invention, the kernel of waste of the rural fruit or of the kernel of the commercial fruit.

Diverse variants are evident of the previous description relative to the different forms of the preparations and uses in particular of the previously mentioned substances, as the portion of fixed total lipids; or the corresponding extracts; or as expression products or the hydrolytic products of the lipids or fractioned isolated products as the oils (free fatty acid and in glycerides forms), included phospholipids as the lecithin, sterols or residues of sterile and acylsteril glycosides extracted of the total fixed lipids of expression of the related "sapotes" and the incorporation in a hydrated lipidic laminar phase of the same lipids of the "sapotes" or partially exchanged with lipids of another origin. The sapogenins and genin also of the "sapotes" can be included as components of the hydrated phase and of the lipidic phase of the hydrated lipidic laminar phases or vesicles of the liposomal type of the previous mention of the "sapotes", which are intimately related with the present invention.

In a variant the hydrated lipidic laminar phase can be of the fixed own lipids of *Calocarpum, Chrysophyllum* or *Lucuma* being able to be transformed the free fatty acid or esterificated of the portion of fixed lipidic in to metallic salts that give them more marked hydrophilic character in ionic state to this fraction.

In accordance with the invention, the lipids used to form the hydrated lipidic laminar phase or the vesicles of the liposomal type are amphiphilic this is that the lipids consist of a molecule possessing a hydrophilic group, which can have ionic or no-ionic character, and a lipophylic group. These amphiphilic lipids are able to form a lipidic laminar phase or vesicle of the liposomal type in presence of a watery phase in accordance with the quantity of water in the mixture. The following ones are among these particular mention lipids: substituted glycerides with phosphoric acid, phospholipids, fosfoaminolipidos, and glycolipids among other. Such substances consist for example, the soy or the egg lecithin, and it can also be the lecithin of the "sapotes" here presented, or the total fraction of phosphatidic lipids of the "sapotes" here demonstrated; mainly the same lipids of the sapotes are used which are recovered as the heavy oleaginous fraction after their specific gravity of *Calocarpum, Chrysophyllum* or *Lucuma* that can be emulsificated with water and form a hydrate lipidic phase conformed by the previously mentioned amphiphilic lipidic compound.

According to the invention it is preferred to use mixture of lipids consisting of at least of a amphiphilic lipid and at least of a hydrophobic lipid like those mentioned previously and next: glycerides as the glyceril oleate, or the glyceril stearate or such sterols as the cholesterol or sitosterol being able to be the "sterols" of the "sapotes", isolated as the colloidal inferior lipidic phase or the fraction of oils as the light lipidic phase regarding their specifies gravity when adding them water that act as hydrophobic lipids. The third fraction here presented of phospholipids that is obtained as the intermediate phase which consists of the amphiphilic lipids that are use here among the total fixed lipids of the "sapotes".

The quantity of hydrophobic lipid expressed in weight won't generally exceed the quantity of the amphiphilic lipid and preferably they won't exceed or decrease in more than a half of this quantity in the formation of the hydrated lipidic laminar phase or of vesicles of the liposomal type.

Even more in one of the most convenient variants in the present work, the concentrations of fixed total lipids, or the oils fraction or the insaponificable lipidic fraction or the phospholipidic fraction or as vegetable total lipidic extracts or as products of lipidic expression or as hydrolytic products of the fixed lipids or as fractional isolated compounds. They are of election from between 0.001% and 100%; and particularly preferable between 0.01 and 99.99% of the weight based on the total weight of the cosmetic or pharmaceutical preparation or of substitutes articles.

These proportions are understood in dry base when it is referred to the lipidic extracts, expression products or hydrolyzed lipidic products or of their fractions or components in isolated form.

In other variants of utility the cosmetic or pharmaceutical dermatological preparations according to the invention also comprise effective quantities of at least some other active selected substance of vitamins particularly A, B, E, and D; L-carnitin; creatin; keratin and their derivatives; ceramidas; thyroxin or their derivatives; pilocarpin; cinchona or their derivatives; derived hidroquinoides; rubefacients as nicotinates; xanthines; ketoconazol; papillary fibroblast supernatants cultures as described in the reference 19; some traces of such elements as the oligoelements chromium, manganese, iron, cobalt, nickel, copper, zinc, molybdenum, selenium, fluoride, chlorine, bromine, iodine, phosphorus, boron, silicon, sulfur; inhibitors of the 5-alpha-reductase such as the progesterone, cyproterone and of Minoxidil®; azelaic acid and their derivatives. Profitably these active substances can be at least partially incorporate in a hydrated lipidic laminar phase or in vesicles of the liposomal type formed by the lipidic (amphiphilic and hydrophobic) substances as the oils, phospholipids and that of residues glycosides of triterpene alcohols ("sterols") coming from the "sapotes" and as the same constituted by hydrated phases composed by solutions or colloidal suspensions of genin and sapogenins, and of their glycosidic ancestors, all related to the "sapotes", being able to be incorporated with the previous active substances.

The cosmetic or pharmaceutical dermatological preparations according to the present invention should be applied topically in particular for the effects delicate defoliation of the cornuem (keratin) superficial layer and the promotion of the gradual invigorated (more that in normal form) renovation of the epidermis, included anti-seborrheic effects and to counteract the effects of the premature deterioration of the skin and of the scalp and the hair; in particular in compositions presented in form of emulsions, creams, gel, solutions, lotions, tonic, shampoos, soaps, skin's softening, astringent, nutritious emulsions, massage creams, make-ups or lengthening stimulant for the lashes, essences, volatile oils, fixed oil, minerals oil, facial handkerchiefs or cleaners, solar agents, tints and colorings; all of local application. It can also have some other substitute's existents or potentials employments of the active substances related to the "sapotes" in this work.

Next some examples of the obtaining are given, characteristic and benefits of topical employments in general as an explanatory mean without implying a restrictive limitation in their widest reaches of some of these examples in the vast uses, obtaining and applications in general of the invention.

In the examples that the units are not indicated they are expressed by percent in weight unless it is indicated some other percentage or unit. In the case of extracts, expression products or hydrolytic products, the percentage is expressed in dry weight.

In the examples 5, 6, 7, 8, 9, 10 and 11 there are implied preparations that contain derived products of the cyanogenic and related structurally similar glycosides, the sapogenins and or genin, of the sapotes that are included by their synergistic effect that they give to the lipidic products of expression and or of lipidic extraction as main constituent isolated fractions or as the whole lipidic portion, in the renovation and development of the skin and in the stimulation of the growth of the hair that also are reasons of this and of another invention by the same author for what is required of consulting the application of related patent all of *Calocarpum, Chrysophyllum* or *Lucuma*.

EXAMPLE 1

Preparation of the fixed lipids of *Calocarpum, Chrysophyllum* or *Lucuma* by expression of the kernels recently dried off.

The fixed lipids of a related specie of *Calocarpum, Chrysophyllum* or *Lucuma* are prepared by the conventional means of a centrifugal grain milling on an endless screw mill coupled with a motor of 0.33 horse power but modified with a thermal device graduated in the squeeze line of the apparatus that reaches temperatures from 80-110° C. with a graduation mean of the temperature, and a form for regulation of the specific exerted pressure. The apparatus is prepared with the molars of the mill for humid grain. The screw of pressure is tight, with at least a pressure of $12.5\pm4.5$ pounds/foot$^2$ ($59.85\pm21.55$ Newton/meter$^2$) and the work exercised by this mechanism of at least 0.33 horses of force or greater.

2 kg are squeezed of fresh, selected kernels, dried off recently and chopped up. In the process of lipidic expression the fixed total lipids (and the vegetable residue of the kernels, after expression or the "crackling") in this way are obtained. The residue of the expression are conserved to be used in the example 2, and later to be used in the obtaining of the cyanogenic glycosides plus related similar glycosides and of their derived genin and sapogenins (that are reason of another application of related patent). The total lipids obtained by expression are filtered on gauze with cotton at temperature from 35 to 100° C., in this way obtained by means the expression process. There are obtained near 800 g. of the refined by filtration fixed total lipids from expression. The solid vegetable residue or residue of the expression (or the "crackling") is conserved for the obtaining of the remainder of fixed lipids left by this process, treated by the subordinate process of lipidic extraction.

EXAMPLE 2

Preparation of the fixed lipids of *Calocarpum, Chrysophyllum* or *Lucuma* by liquid-solid extraction of dry kernels or of the solid residue of lipidic expression.

Preferably dry and milled or crushed kernels are used or the solid vegetable residue of the example 1 ("the crackling"). The solid residue of the expression soaked with a surplus of lipids, or the other kernel-derived materials are treated with an organic non-polar chlorated pure solvent as the methylene chloride purified recently, to give an oils extract.

Preferably of the chlorated solvent mentioned in the previous section are used, as the methylene chloride, 8 kg, as the mean for the liquid extraction and 2 kg of the kernel as the solid to be extracted are used, which are left to reflux for 24 hrs. Then they are filtered at 35 to 100° C. and the filtrate concentrates by distillation at vacuum of the methylene chloride to terminate, to a temperature of at least of 80° C. (b.p. of the methylene chloride is of 40° C., at standard pressure) with that is possible to remove almost entirely this solvent, to give g coming from the dry and milled kernels) of extract of fixed lipids in raw obtained by this extraction process. The purification or refinement of the obtained lipids to the fractions of oils and other components of the extract are carried out like for the example 3, with which the lipids removed of the entire extraction solvent are gotten by means of the treatment with water and anhydrous sodium sulphate which retains the last remainder of the methylene chloride trapped in the humidity present in the lipidic extraction product.

EXAMPLE 3

Obtaining of the oils, of the phospholipids and of the in saponificable fraction of *Calocarpum, Chrysophyllum* or *Lucuma* by centrifugation of the total fixed lipids obtained by expression of the kernels (or by extraction with methylene chloride).

For the purification of the total fixed lipids obtained by the example 1 (or by the example 2), to give the fraction of fixed oils, the fraction of phospholipids and the fraction of insaponificable, continue in the following way.

The total lipidic portion is treated with 50 to 300% (w/v) of water to emulsify it. Then the emulsion is beaked up with centrifugation at 230 to 8,000×g (or greater gravities) for 5 to 45 minutes (or for more prolonged time or repeated) (or by means of free sedimentations, being able to be repeated, for periods that can embrace from 40 to 105 minutes or greater time), continued by the separation of the three formed phases (fraction), continuing with filtrations of the two preponderant fractions obtained separately (individually) as described next.

If is not required this last separation of the oils and phospholipids (lecithins) and the insaponificables fraction the only thing that is required is a filtration through filter paper of thick pore to a temperature from 35 to 100° C. to obtain to the totals fixed lipids acquired by the example 1. For the example 2 if is not required the separation of the oils of the total portion of fixed lipids obtained of this process it's just required the last step of the washes with water and the subsequent treatment with anhydrous sodium sulphate for the removal of the last sludge's of methylene chloride dissolved in the humidity of the fixed lipids.

If the separation of the oils, of the phospholipids fraction and of the insaponificable fraction is required, for the examples 1 and 2, it's recommended to follow the following procedure of isolation, purification and refinement.

1 kg. of the fixed lipids (of expression or extraction) in raw are washed with vigorous agitation with 1 lt. of water being emulsified. It's centrifuged to the same parameters mentioned before, as it was said previously in this example and then the water of the first wash is recovered, to be separated the fraction of insaponificable (or the acrimonious principles) of the total portion of fixed lipids of the example 1 (or optionally for the example 2) as described in the following paragraph of this example. This previous operation is repeated for at least 3 more times with 75% of water each, in respect to the initial weight of the lipids portion, or until it's left the water wash clear without colloidal material suspended, being able to be so with the help of centrifugation to the previous parameters; or by free sedimentation by rests periods during approximately 30 at 120 minutes or more prolonged time (it can be opt for the use of cooling and of heat cycles for the break up of the emulsion, being able to be repeated these whole operations, more than 3 times, using the following mentioned parameters of centrifugation [230 to 8,000×g for 5 to 45 minutes]).

With in the stratification of the centrifugation it's recovered the oleaginous superior phase that corresponds to the fixed oils, later it's continued with the separation of intermediate fraction, to which it's removed the watery inferior liquid, separating in this way the phospholipidic phase (emulsified) suspended in a remainder of clear water. The intermediate phase between the superior initially removed phase of oils and the watery inferior phase is the one corresponding to the phospholipids partially emulsified and that is recovered by its intermediate specific weight and withdraws secondly after the oils. It's separately continued with the treatment of the fixed oil phase and of the phospholipids phase, with filtration between 35 to 100° C. subsequent to the treatment with 200 grs. of anhydrous sodium sulphate in a filter to the same temperature previously mentioned to give a filtrate of fixed oils and another filtrate of the phospholipids included to the lecithins, recovered individually in dry and refined state.

For the fixed lipids obtained by the process of extraction of the example 2, this last treatment eliminates in the water of the washes the remainder of methylene chloride present by dissolution the traces residue of the extract of this example, removing the entirely this solvent by means of the break up in water leaving the fractions of extraction of oils and phospholipids it without the potentially noxious solvent and usable these non "virgin" fractions like in the manufacture of soaps.

The watery phase recovered of the first wash of the total fixed lipids (mainly of the example 1 or optionally of the example 2) contains the residuals triterpenic glycosides or "the sterols" or the fraction in-saponificable, which are recovered by heated (to not more than 90° C.), allowing them to concentrate and later to cool with help of refrigeration, achieving the colloid to sediment. You can use refrigeration, to deposit and afterward decantation the majority of water of filtration in this way removed, for later to be lyophilized the residue or optionally to recover as described next.

You can opt for the extraction with solvent of low or intermediate polarity after the decantation, like with ethers, ketones or esters immiscible with water; such as with petroleum ether, ethyl ether, dimethyl ketone or ethyl acetate and then the extract can be concentrated by evaporation of the solvent to terminate on the recovery of dried fraction extract.

EXAMPLE 4

Transformation of the phospholipids, of *Calocarpum, Chrysophyllum* or *Lucuma* to neuter sodium soaps by the process in cold, useful for the defoliation of the skin.

200 grs of the fixed phospholipids are saponificated, such as obtained for the example 3, being a filtration in hot through thick pore filter paper the only prerequisite to begin the saponification of the phospholipids fraction of the previous example.

40 grs more of tallow is used, the entire lipids are melted and agitated, their allowed to arrive between 30 and 40° C., then 65 ml of bleach (NaOH in water) to approximately a concentration of 35%, are added gradually, with soft agitation. The saponification process begins and the oleaginous mass becomes a uniform opaque mass. Then 12 ml. more of water are added, agitated and then the fragrance is added. At this time and after the entire mixture is agitated. The mass is separated in moulds of appropriate form. It is allowed to complete the saponification in this stage to a temperature of 85° C., until the mass thickens, cool down and dry off.

You can use the soap in the whole body; it's allowed for 1 to 5 minutes of interaction with the foam and then rinsed. The soap is good for daily bathroom use.

EXAMPLE 5

Test for the activity of the fixed total lipids and of the sapogenins of *Calocarpum, (Chrysophyllum* or *Lucuma*) in the renovation of the epidermis.

The test is based on a study of the activity of the products according to the related inventions of the "sapotes" in the cycle of desquamation of the epidermis of 12 subject of both sexes from between 25 to 35 years of age to which are asked to gather the skin of desquamation of their hands for a period of 42 subsequent daily application during 6 days of the week, of the day 1 to day 42 to a dose of 5 ml. of the product supplement that includes the sapogenins.

To approximately regular periods of time, preferably in the mornings, those individuals of test are requested to wash their hands with soft soap, to dry them off, and to apply the products in test in both hands, front and back and to allow to dry of for later to be gather the skin removed by means of the rubbing of the skin, with the last humidity of the supplement product, applied with the same hands, with the purpose of removing the skin of desquamation and putted on a bended linen of clean paper that the individuals in test are provided as stock mean to gather and store in this way the joined desquamation skin scaled during every day of test. All the detritus flaked in the days of test are gathered together. The individuals are asked to gather and after to use ½ gram of the complement product, in test such as obtained in the example 1 of this application that are the total fixed lipids of *Calocarpum*, to be anointed in the suitable indicated region of the hands, until being absorbed entirely. To conclude the final period of the sampling, the identified bent linen with the detritus's are delivered to be studied and to be weighted at the end of the test treatment.

The cells layer of the skin in state of separation of a certain region of the body represented by the weight of the skin flaked in function of the final time of gathering of the sample for each group of individuals and the state of the "alive" skin (epidermis) of the same individuals in test is observed and they are considered in intermediate stages of approximately 10 days and when concluding the sampling in a final recognition.

The study takes place in 12 individuals divided in four groups of 3 individuals each. The first group receives a preparation containing 0.5% of the supplement product of the example 7 of the related application of patent, that includes the mixture of sapogenins of the kernels of Calocarpum (*Chrysophyllum* or *Lucuma*) used as supplement in trial in water; this last one is received as excipient. This first group is also given the lipidic complement in test. The second group receives only the previous mentioned excipient and besides receives the lipidic complement product previously mentioned. The third group receives the sapogenins mixture supplement product alone in the excipient, as the same as for the first group but without receiving the lipidic complement product in test previously mentioned. The fourth group is the control group and received the previous excipient of water (without the sapogenins), and doesn't receives the complement lipidic product previously mentioned.

At the end of the daily scale sample gathering the two groups of individuals (group 1 and 2) are requested to be anointed with ½ gr. of total fixed lipids in test in the same regions of the hand, as the complement product in assay.

The results demonstrate that the keratinocites (corneum cells) difference in desquamation state in a certain region of the body in intermediate stages and at the end of the test manifest to be more marked for the complement of fixed total lipids plus the sapogenins mixture as the supplement products in test (group 1), administration of lipidic complement of the example 1 of this application and of sapogeninic supplement of the example 7 of the related application of patent (ref. 30) respectively of kernels of *Calocarpum*, according to the referred inventions.

In second better test term, of the assays groups, was the one receiving the excipient of water plus the lipidic complement (group 2), because it presented the second best good conditions of the "alive" skin compared against the group that received the supplement with the sapogenins without receiving the lipidic complement (group 3) or the excipient exclusively (group 4), which resulted with the "alive" skin less beneficiated than that of group 1 in advantage in the test that did receives the lipidic complement and the sapogeninic supplement coming from the same vegetable of the related family, caused by the repeated astringent effect of this supplement, excipient with sapogenins and the lubrication absorption effect of the lipidic complement against the control group that didn't receive any sapogeninic product or lipidic.

It is evidenced that the numbers of cells in desquamation state is increased much more quickly in the group that received the sapogenins mixture and the fixed total lipids, according to the related inventions than in the groups receiving the sapogenins exclusively (plus in) and the excipient alone, contrasted against the group receiving the fixed total lipids in test, in disadvantaged without sapogenins supplement; or against the same thing which happens with the control group. It is also observed that the desquamation phase takes place in a soft, subtle, gradual, delicate way for not having daily excessive or marked desquamations with irritations and the effect extends for a longer period in the advantage group receiving the lipidic complement plus the sapogeninic supplement and it is not "interrupted" as markedly as with the other groups, against the control group receiving the excipient of water exclusively in the period of test.

Of the exposed, above-mentioned it is clear that for the most prolonged and more abundant extensions in desquamation phase of the individuals that received the products of *Calocarpum*, (the sapotaceous complement and supplement) according to this invention and to the application of related patent (ref. 30), the fixed total lipids (of the example 1 of this application) and the sapogenins (example 7 of the related application [ref. 30]) respectively, as it was said previously, they increase the percentage of cells in desquamation state and with the consequent renovation of the epidermis, progressively in general and with gradual attenuation of the epidermal external layer visible in the test and in it's repeated use of the sapotaceous products with a gradual and continuous development of the corneous superficial layer that complementarily is attributed to the fixed total lipids in test (plus to the Sapotaceous sapogenins supplementary administered).

It is concluded because the best state in the "alive" skin of the individuals tried with the products in test, which are the fixed total lipids and the sapogenins of the related genus of the family Sapotaceae that exists a synergic beneficial activity in the apply conditions in the epithelial system. It is inferred that the dynamism and the mechanism of balance regulation among the quantity of keratinocites that are flaked and of cells that enter in mitosis that assure the constant thickness of the epidermis leans toward a gradual attenuation under soft, subtle and delicate conditions of reaction among the related products in test in relatively young individuals and the region of the skin application in the desquamation, in the daily repeated use, with stimulation of the development of the skin (Cordero A. A. 1996, Biologia de la Piel, Ed. Pan-American p. 27-28).

Several examples of formulations of cosmetics and of pharmaceuticals compositions that promote the renovation and the growth/development of the epidermis and the hair are exposed in the following examples.

EXAMPLE 6

Preparation of an Anti-Wrinkle Cream
The following compositions are prepared.

| Composition A: | |
|---|---:|
| Total fixed lipids of *Calocarpum*, (*Chrysophyllum* or *Lucuma*) as obtained in the example 1 of this application. | 20.0 |
| Lanolin | 10.0 |
| Isopropyl Palmitate | 3.0 |
| Concentrated solution of vitamin A and D | 1.0 |
| Yellow wax | 7.5 |
| Butylated hydoxyanisole (BHA) | 0.002 |
| Composition B: | |
| Trietanolamine | 1.0 |
| Water | 53.0 |
| Carbomer (carbopol 934 ®) | 0.33 |
| Glycerine | 3.0 |
| Perfume | 0.4 |
| Sapogenins of *Calocarpum*, such as obtained of the example 7 of the application of related patent (ref. 30). | 0.4 |

The gel is prepared which uses a watery solution of 0.3% of sapogenins of *Calocarpum*, which gets ready suspending 0.33 g. of carbopol 934® (carbomer) predisposed in the conventional way and it is used in the preparation of the composition B.

Warm up composition A and B independently to 75° C. and the composition B is added to the composition A, slowly with continuous agitation. The agitation is continued and then the perfume is added to 35° C.

EXAMPLE 7

Use of the fixed total lipids and genin of *Calocarpum*, in the preparation of a hydrated lipidic laminated phase for a liposomal cosmetic.

Solubilize 0.3 g. of genin, in 9.0 g. of the mixture of total fixed lipids of *Calocarpum* such as obtained in the example 1 of this application and the resulting mixture is agitated until the solubilization has taken place. Warm up to 60° C. for 1 hour in a rotational flask of evaporation.

The lipidic tunic deposited in the internal walls of the flask separates with 40.6 g. of distilled water and the mixture becomes agitated for three hrs. to ambient temperature. Then the homogenization is finished and the vesicular formation acquired to a temperature of 4° C. The vesicles obtained are of uniform size.

Preferably this liposomas suspension is gelled with the mixture of 50.0 g. of a gel of 1.25% carbomer.

EXAMPLE 8

Preparation of a liposomal biphase containing sapogenins and "lecithins" of *Calocarpum*, (*Chrysophyllum* or *Lucuma*).

0.4 g. of the sapogenins mixture are solubilized in 10 ml. of methanol and are added to 5 g. of a mixture of phospholipids (lecithins) of *Calocarpum*, such as obtained in the example 3 of this application and cholesterol in a proportion in weight of 9:1 and the resulting mixture becomes agitated until you solubilize it, warms it to 68° C. for 1 hour in a rotational flask of evaporation.

The tunic of lipids deposited in the internal walls of the flask are mixed with 44.6 g. of distilled water and the mixture becomes agitated for 3 hrs. to ambient temperature. It's homogenized for 20 minutes more. The obtained vesicles are of uniform size.

Preferably this liposomas suspension is gelled by the mixture of 50.0 g. of a gel of 1.25% carbomer.

It can be notice that the composition can have variable proportions of the extracts or products of Calocarpum (*Chrysophyllum* or *Lucuma*) and they can be obtained in function of the dilution taken on account, which constitutes a particularly easy way of other new proportional creations.

EXAMPLE 9

Preparation of an anti-wrinkles liposomal cream containing in the liposomal laminar phase total fixed lipids plus sapogenins and in the watery external phase also sapogenins, all of *Calocarpum* (*Chrysophyllum* or *Lucuma*).

9.4 g of the mixture of lipids of *Calocarpum* obtained as the total fixed lipids of the example 1 of this application, are transformed to a temperature of 60° C., in a dispersion with magnetic agitation in a watery prepared suspension, dispersing of 1.2 g of the sapogenins mixture in 89.4 g of water. The agitation stays for 2 hrs. to the same temperature after which the mixture is homogenized with a mechanical agitator until reaching a temperature of 4° C. for 10 min. In this way vesicles of uniform size are obtained.

Preferably this liposomas suspension is gelled for the blended with 100 g of a gel to 1.25% of carbomer 940 prepared in the conventional way separately. This gives 200 g of a gelled liposomal suspension partially "encapsulating" a mixture of sapogenins of *Calocarpum* in a lipidic laminated phase formed by the same total fixed lipids of the example 1 of this application. The concentration of the sapogenins is of 0.6% based on the total weight of the suspension.

One can notice that the composition can have variable proportions of the extract or of the products of *Calocarpum* (*Chrysophyllum* or *Lucuma*) and they can be obtained in function of the accounted dilution.

EXAMPLE 10

Oleate for the Treatment of Seborrheic Alopecia
The following composition is prepared:

| | |
|---|---:|
| Sapogenins of *Calocarpum* (*Chrysophyllum* or *Lucuma*), such as obtained in the example 7, of the application of related patent. | 1.0 |
| Genin of *Calocarpum*, *Chrysophyllum* or *Lucuma*, | 0.4 |
| Quinine hydrochloride | 1.8 |
| Pilocarpine nitrate | 0.5 |
| Propylene glycol | 10.0 |
| Alcohol 20% | 10.0 |
| Isopropyl myristate | 20.0 |
| Total fixed lipids of *Calocarpum*, *Chrysophyllum* or *Lucuma* as obtained in the example 1 of this application. | 56.3 |

The preparation is warmed in a hot water bath with, it is homogenized and it is applied in the hairy scalp and without being carved it is allowed for 15 min. of interact in the damaged hairy scalp. After the contact of the preparation with the skin and the hair it can be wash with water and a soft soap or shampoo.

EXAMPLE 11

Treatment cream to combat cutaneous senescence.

| Composition A: | |
|---|---:|
| Fixed Oil of *Calocarpum* (*Chrysophyllum* or *Lucuma*), as obtained in the example 3 of this application. | 19.2 |
| Spermaceti | 5.3 |
| Isopropyl myristate | 1.9 |

-continued

| | |
|---|---|
| Butylhydroxytoluene (BHT) | 0.005 |
| Propyl gallate | 0.005 |
| Composition B: | |
| Borax | 1.7 |
| Demineralised water | 14.9 |
| Sodium stearate | 1.9 |
| Propylene glycol | 5.3 |
| Composition C: | |
| Sapogenins of *Calocarpum* (*Chrysophyllum* or *Lucuma*), | 0.50 |
| Sodium carboxymethylcelulose | 0.37 |
| Demineralised water | 47.4 |
| Composition D: | |
| Hydroquinone | 0.8 |
| Genin of *Calocarpum* (*Chrysophyllum* or *Lucuma*), | 0.1 |
| Fragrances | 0.3 |

Warm the composition A, to 80° C. Make the following two mixtures independently each one from the other to the previous same temperature. For the composition B, mix the propylene glycol more sodium stearate and the sodium borate in the water, and they are added respectively with agitation and homogenization to the composition A. The compositions C gets ready dissolving the sapogenins of *Calocarpum, Chrysophyllum* or *Lucuma* in the water of this composition and then gelled with the sodium carboxymethylcelulose. Then warm the obtained gel to the previous same temperature and add with agitation to the previous preparation. To conclude the heating it's allowed to cool down to 25° C. and then adding the composition D that has been integrated previously to each other and the homogenization gets finishes to 4° C.

REFERENCES

1.—Morton, J.; Sapote, Canistel, Lucmo, Star Apple. In: Fruits of Warm Climates, (1987) p. 397-410. http://newcrop.hort.purdue.edu/newcrop/morton/sapote_ars.html
2.—*Lucuma* . . . *Lucuma*! Peru's favorite ice cream flavor! *Lucuma* fruit *Lucuma obovata* HBK) http://www.tjpmd.com/lucma.htm
3.—Tico Ethnobotanical Dictionary http://www.ars-grin.gov/duke/dictionary/tico/f.html
4.—Document U.S. Pat. No. 5,723,149 (1998) Use of Medicago Saponins for the Preparation of Cosmetic or Pharmaceutical Compositions, Especially Dermatological Compositions, Promoting Renewal of the Epidermis, Stimulating Hair Regrowth or Delaying Hair Loss.
5.—Herber, V. (1979) Laetrile: The Cult of Cyanide. Promoting Poison for Profit. Am. J. Clin. Nutr. 32, 112-1158.
6.—Morera, J. A. (1994) Sapote (Pouteria sapota). In: Neglected Crops: 1492 From a Different Perspective. Bermejo, J. E. H. y León, J. (eds.) Plant Production Protection Series No 26 FAQ, Rome, Italy. p. 103-107.
7.—Lambert, M. y Crane, J. H. (1990) Mamey Sapote. In: Tropical Fruits p. 337-355. Advances in New Crops. Timber Press, Portland, Ed. J. Janick and J. E. Simon.
8.—Allen Ph. (1943) Poisonous and Injurious Plants of Panama. America Journal of Tropical Medicine 23(suppl.) p. 3-76.
9.—José Luis Diaz (1976) In: Índice y Sinonimia de las Plantas Medicinales de México, Monografira Científica I y II, IMEPLAM A. C.
10.—Whitman, W. F. (1966) The Green Sapote a New Fruit for South Florida, Proc. Fla. State Hort. Soc. Proc. (1965), 78, 330-336
11.—Pouteria sapote. Pouteria sapote Acc. 199800087 URL: http://florawww.eeb.uconn.edu/PalmWeb/199800087.html
12.—"Free Book", anonymous author (1989); Lost Crops of the Incas Little-Known Plants of the Andes with Promise for Worldwide Cultivation p. 263-266. National Academy Press. http://books.nap.edu/books/030904264x/html/270.html‡‡pagelop
13.—Document U.S. Pat. No. 4,557,853 (1985) Skin Cleansing Compositions Containing Alkaline Earth Metal Carbonates As Skin Feel Agents.
14.—Campbell, R. J. (1996); SAPOTACEAE In: South America Fruits Deserving Further Attention. http://www.hort.purdue.edu/newcrop/proceedings1996/v3-431.html
15.—REMINGTON Farmacia; Gennaro A. R. editor; $19^a$ ed. Tomo 1 y 2 Editorial Medica Panamericana, 1995 p. 561, 562, 558, 929 y 2418.
16.—Merfort, I. (1984). Phytochemical Study of *Lucuma mammosa*. Fitoterapia 55(4): 316-317.
17.—Ansell, G. B. y Hawthorne, J. N. (1964); *Phospholipids* In: Elsevier, N.Y.,; p. 439.
18.—Eichberg, J. "*Fats and fatty oils*" p. 795-831, vol. 9 "*Lecithin*" p. 250-269, vol. 14. In: Kirk-Othmer Encyclopedia of Chemical Technology; Wiley-Interscience, New York $3^a$ ed. 1981;
19.—Document EP-A-272 920
20.—Poucher, W. A. Revised by Haward, G. M. (1984) Soap Perfumery. En: Perfumes, Cosmetics and Soaps Vol. II, The Production, Manufacture and Application of Perfumes. Published by Chapman and Hall Ltd. $8^a$ ed. London, N.Y.
21.—Seigler, D. S. (1975); Isolation and Characterization of Naturally Occurring Cyanogenic Compounds. *Phytochemistry* 14, 9-29.
22.—Document U.S. Pat. No. 6,124,362 (2000) Method for Regulating Hair Growth.
23.—Document U.S. Pat. No. 4,621,023 (1986) Method of Homogenizing Dispersions of Hydrated Lipidic Lamellar Phases and Suspensions Obtained by the Said Method.
24.—Document U.S. Pat. No. 4,508,703 (1985) Production of Pulverulent Mixtures of Lipidic and Hydrophobic Constituents.
25.—Eyjolfsson R. (1971); Constitution and Stereochemistry of Lucumin, a Cyanogenic Glycoside From *Lucuma mammosa* Gaertn. Acta Chem. Scand. 25(5), 1898-900.
26.—The New York Botanical Garden. URL: http://www.nybg.org/bsci/hcol/wivasc/sapotaceae.html or http://www.nybg.org/bsci/hcol/vas/Sapotaceae.html.
27.—Zúñiga, R. J. (1981); Semillas Oleaginosas del Trópico Americano. *Arch. Latinoam. Nutr*. XXXI, (2) 350-369.
28.—Munguia, R. R., Millares, N. F. (1949); Fixed Oils of México. *JAOCS,* 26, 434.
29.—Itoh, T., Tamura, T., Iida T., Matsumoto T. (1974); Gas Chromatographic Differentiation of 4-Desmethyl, 4-Monomethyl and 4,4-Dimethylsterols. *Steroids,* 23(5) 687-694.
30.—De la Llata, R. L.; Obtención de los Glicósidos Cianogénico y Relacionados más Derivados Genin y Sapogenins de Plantas de la, amilia Sapotácea para la Preparación de Cosméticos y Composiciones Dermatológicas. Patent Application, Mexico (June 2004) PCT/MX 2004/00052.
31.—Willuhn, G., Merfort, I., Matthiesen, U. (1983); The Occurrence of Lanosterol and 24-Methylenelanost-8-en-3β-ol in Leaves of *Symphoricarpus albus. Phytochemistry* 22(1) 137-141.

32.—Budzikiewicz, H., Wilson, J. M., Djerassi, C. (1963); Mass Spectrometry in Structural and Stereochemical Problems. XXXII. Pentacyclic Triterpenes. *J. Am. Chem. Soc.* 85, 3688-3699.

33.—Argueta, V. A., Cano, A. L. M., Rodarte, M. E.; In: Atlas de las Plantas de la Medicina Tradicional Mexicana. I.N.I. (1994).

34.—Pennigton, T. D., Sarukhan, J.; In: Árboles Tropicales de México. Fondo de Cultura Económica 2$^a$ ed. (1998).

35.—Bondioli, P. et al. (1996); Caratterizzazione Chimica del Seme di Zapote (*Lucuma mammosa*). *La Rivista Italiana delle Sostanze Grasse.* 73(5)229-230.

What is claimed is:

1. A process for obtaining fractions of a concentrate of total fixed lipids from an expression of kernels of the family Sapotaceae, the process comprising the steps of:
    a) subjecting the kernels to a pressure of 38.30-81.40 Newton/meter$^2$, equal to 8-17lb/ft$^2$ at a temperature from 80 to 110° C.;
    b) filtering a liquid obtained in the step a) at a temperature between 35 to 100° C.;
    c) recovering a filtered liquid portion, comprising the concentrate of total fixed lipids from the expression of kernels of the family Sapotaceae, and a solid fraction portion retained and left apart, that are obtained from the filtering as set forth in step b) separately; and
    d) separating the filtered liquid portion comprising the concentrate of total fixed lipids from the expression of kernels of the family Sapotaceae into a superior fraction A of an oil, an intermediate fraction B of phospholipids and an inferior fraction C of glucosidic triterpenes and of the sterols by the process comprising the steps of:
    1) adding from 50 to 300% of water to the concentrate of total fixed lipids and emulsifying it in one or three more subsequent parts;
    2) subjecting the emulsion to at least a centrifugation cycle for 5 to 45 minutes at 1,000 to 6,000 rpm approximately in a rotor of 20.5 cm of radial distance or equivalent, expressed in relative gravitational force g, for a gram of homgenate, from 230 to 8,000×g or bigger, from 5 to 45 minutes or for more prolonged times;
    3) separating the superior fraction A of step 2) which corresponds to the oils;
    4) separating the intermediate fraction B of the step 2) which corresponds to the phospholipids;
    5) separating the inferior fraction C of the step 2) which corresponds to the residues of glucosidic triterpenes and of sterols in a watery medium; and
    6) subjecting the inferior fraction C of residues of glucosidic triterpenes and of sterols in the watery-medium to separation by refrigeration, sedimentation, and centrifugation to decant the water and lyophilize the watery sediment or by precipitation with agents or with an extraction using a solvent selected from intermediate polarity, immiscible as alkanes, ketones, esters or ethers of low molecular weight, as petroleum ether, chloroform, acetone, ethyl methyl ketone, ethyl acetate or ethyl ether, with which an organic phase is recovered which is subjected to evaporation to recover this fraction as semi-purified dry extract, where all these lipidic fractions, fraction A, fraction B and fraction C, are free of toxic substances.

2. The process of the claim 1, where the step a) is carried out in a centrifugal mill of endless screw coupled with a motor of 0.33 horsepower or bigger, modified, with a thermal graduate device that reaches temperatures from 80 to 110° C.

3. The process of obtaining of concentrate in accordance with claim 1 where a yield of total fixed lipids is from 35 to 95% of the total content of lipids of the kernels.

4. The process of the claim 1, wherein the concentrate of total fixed lipids obtained by the process comprises from 40 to 70% of oils, from 30 to 60% of phospholipids and from 0.1 to 1% of residues glucosidic triterpenes and of sterols of the total content of lipids of the concentrate obtained by the expression of the kernels, and the concentrate is free of toxic substances.

5. The superior fraction A, of oils of the concentrate of total fixed lipids of kernels of the family Sapotaceae obtained by the process of the claim 1.

6. The intermediate fraction B, of phospholipids of the concentrate of total fixed lipids of kernels of the family Sapotaceae obtained by the process of the claim 1.

7. The inferior fraction C, of residues of glucosidic triterpenes and of sterol of the concentrate of total fixed lipids of kernels of the family Sapotaceae obtained by the claim 1.

8. The process of claim 1 where the kernels are selected of the family Sapotaceae of the species *Calocarpum sapota, Calocarpum mammosum, Calocarpum viride, Lucuma domingensis, Lucuma salicifolia, Lucuma obovata, Lucuma hypoglauca, Chrysophyllum mexicanum* or *Chrysophyllum caimito*.

\* \* \* \* \*